United States Patent [19]

Stroech et al.

[11] Patent Number: 5,126,359

[45] Date of Patent: * Jun. 30, 1992

[54] SUBSTITUTED BISAZOLES AND THEIR USE AS MEDICAMENTS

[75] Inventors: Klaus Stroech, Solingen; Susanne Backens-Hammerschmidt, Bergisch-Gladbach; Manfred Plempel, Haan, all of Fed. Rep. of Germany

[73] Assignee: Bayer Aktiengesellschaft, Leverkusen, Fed. Rep. of Germany

[*] Notice: The portion of the term of this patent subsequent to Oct. 24, 2006 has been disclaimed.

[21] Appl. No.: 422,827

[22] Filed: Oct. 17, 1989

[30] Foreign Application Priority Data

Nov. 4, 1988 [DE] Fed. Rep. of Germany ....... 3837463

[51] Int. Cl.$^5$ .................. A61K 31/41; C07D 249/08
[52] U.S. Cl. ................... 514/383; 548/266.6
[58] Field of Search .............. 514/383, 397; 548/266.6, 110, 376

[56] References Cited

U.S. PATENT DOCUMENTS

| | | | |
|---|---|---|---|
| 4,599,424 | 7/1986 | Driscoll | 548/140 |
| 4,870,088 | 9/1989 | Blume et al. | 514/383 |
| 4,875,928 | 10/1989 | Regel et al. | 514/383 |
| 4,910,213 | 3/1990 | Regel et al. | 514/383 |
| 4,960,781 | 10/1990 | Holmwood et al. | 548/266.2 |

FOREIGN PATENT DOCUMENTS 0122693 10/1984 European Pat. Off.
0164246 12/1985 European Pat. Off.

OTHER PUBLICATIONS

Burger, "Medicinal Chemistry" 2nd Ed. N.Y., 1960, p. 1055.

*Primary Examiner*—Patricia L. Morris
*Attorney, Agent, or Firm*—Sprung Horn Kramer & Woods

[57] ABSTRACT

Antimycotically active azolyl-cyclopropyl-azolylmethylcarbinol compound of the formula $$\begin{array}{c} \text{OR}^1 \\ | \\ \text{R}^2-\text{C}-\text{C} \\ | \quad \diagdown / \\ \text{CH}_2 \quad \text{N} \\ | \\ \text{N} \diagdown_{\text{Y}} \\ \| \\ \text{N} \end{array} \begin{array}{c} \text{N} \\ \diagup \diagdown \\ \quad \quad \text{X} \\ \diagdown_{\text{N}} \end{array}$$

in which $R^1$ - represents hydrogen, or alkyl which is optionally substituted by optionally substituted aryl or
- represents alkenyl or alkynyl or trialkylsilyl or alkylcarbonyl, $R^2$ - represents optionally substituted aryl or
- represents an optionally substituted 5- to 6-membered heterocycle which may contain one or more heteroatoms such as sulphur, oxygen or nitrogen, X - represents halogen, and
Y - represents a nitrogen atom or the CH group, and their acid addition salts.

10 Claims, No Drawings

SUBSTITUTED BISAZOLES AND THEIR USE AS MEDICAMENTS

The present invention relates to new substituted 1-[1-(3-chloro-1,2,4-triazol-1-yl)-cyclopropyl]-2-(1,2,4-triazol-1-yl)-ethan-1-ol derivatives, processes for their preparation and their use as medicaments, in particular as antimycotics.

It has already been disclosed that certain diazolyl derivatives and substituted azolylcyclopropylazolylmethyl-carbinol derivatives possess good antimicrobial, in particular antimycotic, properties [compare EP-OS 0,044,605 and DE 3,440,114 Al]. However, the action of these substances is not always completely satisfactory in all indication areas.

New substituted azolyl-cyclopropyl-azolylmethyl-carbinols of the general formula (I)

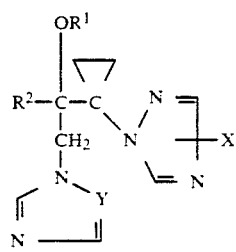
(I)

in which

R$^1$ - represents hydrogen or
- represents straight-chain or branched alkyl having up to 8 carbon atoms which is optionally substituted by aryl which, in turn, is substituted by halogen, C$_1$-C$_8$-alkyl, C$_1$-C$_8$-alkoxy, C$_1$-C$_8$-alkylthio, C$_1$-C$_8$-halogenoalkyl, C$_1$-C$_8$-halogenoalkoxy, C$_1$-C$_8$-halogenoalkylthio or by phenyl which is optionally monosubstituted to tetrasubstituted by identical or different substituents or
- represents straight-chain or branched alkenyl or alkynyl having up to 8 carbon atoms or
- represents trialkylsilyl having up to 8 carbon atoms in the alkyl moiety or
- represents alkylcarbonyl having up to 8 carbon atoms in the alkyl moiety, R$^2$ - represents aryl having 6 to 10 carbon atoms which is optionally monosubstituted to tetrasubstituted by identical or different substituents from the series comprising halogen, C$_1$-C$_8$-alkyl, C$_1$-C$_8$-alkoxy, C$_1$-C$_8$-alkylthio, or by halogenoalkyl, halogenoalkoxy or halogenoalkylthio having up to 8 carbon atoms in the alkyl moiety, where the halogen atoms are identical or different or may be substituted by phenyl, phenylthio or phenoxy which, in turn, may be monosubstituted to trisubstituted by identical or different halogen substituents, or
- represents a 5- to 6-membered heterocycle which may contain one or more heteroatoms such as sulphur, oxygen or nitrogen and which is optionally substituted by halogen, C$_1$-C$_8$-alkyl, C$_1$-C$_8$-alkoxy, C$_1$-C$_8$-alkylthio or by halogenoalkyl, halogenoalkoxy or halogenoalkylthio having up to 8 carbon atoms in the alkyl moiety, X - represents halogen, and
Y - represents a nitrogen atom or the CH group, and their acid addition salts have now been found.

Salts of the compounds according to the invention are addition products with acids. The acids which can be added preferably include physiologically tolerable acids, in particular hydrohalic acids, such as, for example, hydrochloric acid and hydrobromic acid, in particular hydrochloric acid, and in addition phosphoric acid, nitric acid, sulphuric acid, mono- and bisfunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid.

Preferred compounds are those of the general formula (I) in which

R$^1$ - represents hydrogen or
- represents straight-chain or branched alkyl having up to 6 carbon atoms which is optionally substituted by phenyl which, in turn, may be substituted by halogen, C$_1$-C$_6$-alkyl, C$_1$-C$_6$-alkoxy, C$_1$-C$_6$-alkylthio, C$_1$-C$_6$-halogenoalkyl or by phenyl which is optionally monosubstituted to trisubstituted by identical or different halogen substituents, or
- represents straight-chain or branched alkenyl or alkynyl having up to 6 carbon atoms or
- represents trialkylsilyl having up to 6 carbon atoms in the alkyl moiety or
- represents alkylcarbonyl having up to 6 carbon atoms in the alkyl moiety, R$^2$ - represents phenyl or naphthyl which is optionally monosubstituted to trisubstituted by identical or different substituents from the series comprising halogen, C$_1$-C$_6$-alkyl, C$_1$-C$_6$-alkoxy, C$_1$-C$_6$-alkylthio or by halogenoalkyl, halogenoalkoxy or halogenoalkylthio having up to 6 carbon atoms in the alkyl moiety, where the halogen atoms are identical or different, or by phenyl, phenylthio or phenoxy which, in turn, may be monosubstituted or disubstituted by identical or different substituents from the series comprising fluorine, chlorine or bromine, or
- represents a 5- to 6-membered heterocycle which may contain one or more heteroatoms such as sulphur, oxygen or nitrogen and which is optionally substituted by halogen, C$_1$-C$_6$-alkyl, C$_1$-C$_6$-alkoxy, C$_1$-C$_6$-alkylthio or by halogenoalkyl, halogenoalkoxy or halogenoalkylthio having up to 6 carbon atoms in the alkyl moiety,
- X represents halogen, and
Y - represents a nitrogen atom or the CH group, and their acid addition salts.

Particularly preferred compounds are those of the general formula (I) in which

R$^1$ - represents hydrogen or
- represents straight-chain or branched alkyl having up to 4 carbon atoms which is optionally substituted by phenyl which, in turn, may be substituted by fluorine, chlorine, bromine, C$_1$-C$_4$-alkyl, C$_1$-C$_4$-alkoxy, C$_1$-C$_4$-alkylthio, C$_1$-C$_4$-halogenoalkyl or by phenyl which is optionally monosubstituted or disubstituted by identical or different substituents from the series comprising fluorine, chlorine or bromine, or
- represents straight-chain or branched alkenyl or alkynyl having up to 4 carbon atoms or
- represents trialkylsilyl having up to 4 carbon atoms in the alkyl moiety or
- represents alkylcarbonyl having up to 4 carbon atoms in the alkyl moiety, $R^2$ - represents phenyl or naphthyl which is optionally monosubstituted or disubstituted by identical or different substituents from the series comprising fluorine, chlorine, bromine, $C_1$-$C_4$-alkyl, $C_1$-$C_4$-alkoxy, $C_1$-$C_4$-alkylthio or by halogenoalkyl, halogenoalkoxy or halogenoalkylthio having up to 4 carbon atoms in the alkyl moiety, where the halogen atoms may be identical or different, or by phenyl, phenoxy or phenylthio which, in turn, may be substituted by fluorine, chlorine or bromine,

- represents a 5- to 6-membered heterocycle which may contain one or more heteroatoms such as sulphur, oxygen or nitrogen and which is optionally substituted by fluorine, chlorine, bromine, $C_1$-$C_4$-alkyl, $C_1$-$C_4$-alkoxy, $C_1$-$C_4$-alkylthio or by halogenoalkyl, halogenoalkoxy or halogenoalkylthio having up to 4 carbon atoms in the alkyl moiety, X - represents fluorine, chlorine or bromine and Y - represents a nitrogen atom or the CH group, and their acid addition salts.

The substances according to the invention contain an asymmetric substituted carbon atom. They may therefore be obtained in optically isomeric forms. The present invention relates both to the individual isomers and to their mixture.

The compounds of the general formula (I) according to the invention and their acid addition salts show good antimicrobial, in particular antimycotic, properties.

The compounds of the general formula (I) according to the invention

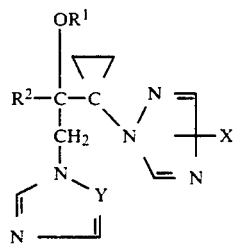

(I)

in which $R^1$, $R^2$, X and Y have the abovementioned meaning, can be prepared according to known methods by

[A] first reacting halogenated azolylcyclopropyl ketones of the general formula (II)

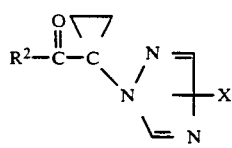

(II)

in which $R^2$ and X have the abovementioned meaning, with dimethylsulphonium methylide or dimethyloxosulphonium methylide of the formula (III)

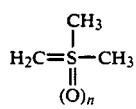

(III)

in which n - denotes a number 0 or 1, in the presence of a diluent, such as, for example, dimethyl sulphoxide, at temperatures between +20° C.
and +80° C. [compare for this purpose J. Am. Chem. Soc. 87, 1363–1364 (1965)] to give compounds of the general formula (IV)

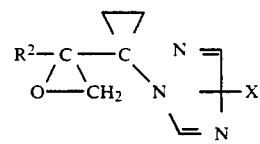

(IV)

in which $R^2$ and X have the abovementioned meaning, and then reacting with azoles of the general formula (V)

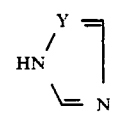

(V)

in which

Y has the abovementioned meaning, in the presence of an inert organic solvent, such as, for example, acetonitrile or dimethylformamide, in the presence of a base, such as, for example, potassium carbonate or potassium hydroxide, at temperatures between +40° C. and +150° C. to give compounds of the general formula (Ia)

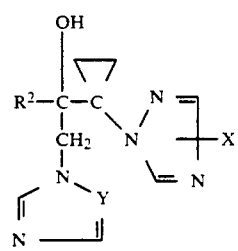

(Ia)

in which $R^2$, X and Y have the abovementioned meaning, and then converting in the presence of a diluent into the corresponding alkoxide and reacting this with compounds of the general formula (VI)

(VI)

in which $R^1$ has the abovementioned meaning, and $Z^1$ - represents chlorine, bromine or iodine, in the presence of an inert organic solvent, such as, for example, ethers or chlorinated hydrocarbons, at temperatures between 0° C. and +100° C., or by

[B] first reacting diazolyl ketone derivatives of the general formula (VII)

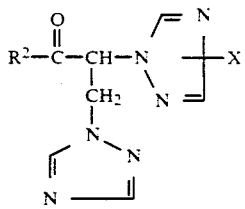  (VII)

in which

R² and X have the abovementioned meaning,
with at least a three-fold equivalent amount of dimethyloxosulphonium methylide of the formula (IIIa)

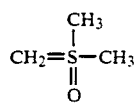  (IIIa)

according to the method indicated under variant [A] and reacting the corresponding hydroxy compounds in turn via the corresponding alkoxides with compounds of the general formula (VI) in the manner indicated under [A].

In a preferred embodiment of the reaction of the compounds of the general formula (Ia), the process is expediently carried out so that these are converted by means of alkali metal hydride or alkali metal amide in a suitable organic solvent into the alkali metal alkoxide and the latter is reacted immediately without isolation with a halide of the formula (VI), the compounds of the formula (I) being obtained in one operation with the elimination of alkali metal halide.

According to a further preferred embodiment of this reaction step, the preparation of the alkoxides and the alkylation are expediently carried out in a two-phase system, such as, for example, aqueous sodium hydroxide solution/toluene or potassium hydroxide solution/toluene or methylene chloride, with the addition of 0.01 to 1 mole of a phase transfer catalyst, such as, for example, ammonium or phosphonium compounds, the alkoxides and being reacted in the organic phase or on the boundary surface with the halides present in the organic phase.

The acid addition salts of the compounds of the formula (I) may be obtained in a simple manner by customary salt formation methods, for example by dissolving a compound of the formula (I) in a suitable inert solvent and adding the acid, for example hydrochloric acid, and may be isolated in a known manner, for example by filtering off, and, if desired, may be purified by washing with an inert organic solvent.

The aryl azolylcyclopropyl ketones of the general formula (II) are new. They may be obtained by reacting aryl halogenopropyl ketones of the general formula (VIII)

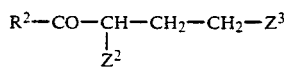  (VIII)

in which

R² has the abovementioned meaning
and

Z² and Z³ are identical or different and preferably represent bromine or chlorine, with azoles of the general formula (IX)

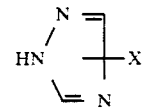  (IX)

in which X has the abovementioned meaning, in the presence of an inert organic solvent, such as, for example, acetonitrile or dimethylformamide, in the presence of a base, such as, for example, potassium carbonate or potassium hydroxide, at temperatures between +40° C. and +150° C.

The dimethyloxosulphonium methylide of the formula (III) employed as starting material is produced in situ by reaction of trimethyloxosulphonium iodide with sodium hydride or sodium amide, in particular with sodium tert. butoxide or sodium methoxide, in the presence of a diluent.

The azoles of the general formula (V) and (IX) are known [compare K. Schofield, M. R. Grimmett, B. R. T. Keene, "The Azoles", Cambridge University Press, Cambridge 1976].

The compounds of the general formula (VIII) are known or can be prepared by known methods [compare DE-OS (German Published Specification) 2,521,104, DE-OS (German Published Specification) 2,320,355 and DE-OS (German Published Specification) 2,351,948].

The diazolyl-keto derivatives of the general formula (VII) are new and can be prepared by reacting compounds of the general formula (X)

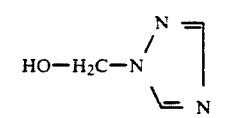  (X)

in which

R² and X have the abovementioned meaning,
with hydroxymethylazoles of the general formula (XI)

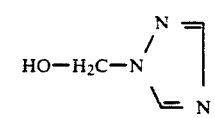  (XI)

in the presence of an inert organic solvent, such as, for example, toluene, and in the presence of a catalyst, such as, for example, piperidine acetate, preferably at the boiling point of the solvent used.

The compounds of the general formula (X) can be prepared in a generally customary manner [compare DE-OS (German Published Specification) 2,431,407; DE-OS (German Published Specification) 2,610,022 and DE-OS (German Published Specification) 2,638,470)].

The compound of the formula (XI) is also known [compare EP 0,006,102 and Chem. Heterocycl. Comp. 1980, 189].

The compounds of the general formula (VI) are generally known compounds of organic chemistry [C. Ferri, Reaktionen der organischen Synthese (Reactions of Organic Synthesis), Georg Thieme Verlag, Stuttgart, 1978].

The compounds of the formula (I) utilizable according to the invention and their acid addition salts exhibit antimicrobial, in particular strong antimycotic, actions. They possess a very wide antimycotic spectrum of action, in particular against dermatophytes and Blastomycetes and also biphasic fungi, for example against Candida species, such as Candida albicans, Epidermophyton species, such as Epidermophyton floccosum, Aspergillus species, such as Aspergillus niger and Aspergillus fumigatus, Trichophyton species, such as Trichophyton mentagrophytes, Microsporon species, such as Microsporon felineum and also Torulopsis species, such as Torulopsis glabrata. The innumeration of these microorganisms in no case represents a limitation on the microorganisms which can be combated, but is only of illustrative character.

Examples of indications in human medicine which may be mentioned, for example, are: dermatomycoses and systemic mycoses caused by Trichophyton mentagrophytes and other Trichophyton species, Microsporon species, Epidermophyton floccosum, Blastomycetes and biphasic fungi and also Hyphomycetes.

Areas of indication which may be mentioned in veterinary medicine, for example, are: all dermatomycoses and systemic mycoses, in particular those which are caused by the abovementioned pathogens.

The present invention includes pharmaceutical preparations which contain one or more active compounds according to the invention or which consist of one or more active compounds according to the invention in addition to non-toxic, inert pharmaceutically suitable excipients, and a process for the production of these preparations.

The present invention also includes pharmaceutical preparations in dosage units. This means that the preparation is present in the form of individual parts, for example tablets, coated tablets, capsules, pills, suppositories and ampoules whose content of active compound corresponds to a fraction or a multiple of a single dose. The dosage units may contain, for example, 1, 2, 3 or 4 individual doses or ½, ⅓ or ¼ of an individual dose. An individual dose preferably contains the amount of active compound which is administered in one administration and which usually corresponds to a whole, a half, a third or a quarter of a daily dose.

Non-toxic, inert pharmaceutically suitable excipients are taken to mean solid, semi-solid or liquid diluents, fillers and formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders and sprays.

Tablets, coated tablets, capsules, pills and granules may contain the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium carbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example, talc, calcium stearate and magnesium stearate and solid polyethylene glycols or mixtures of the substances mentioned under (a) to (i) in addition to the active compound or compounds.

The tablets, coated tablets, capsules, pills and granules may be provided with the customary coatings and coverings, optionally containing opacifying agents, and may also be composed so that they optionally release the active compound or compounds in a sustained manner, only or preferably in a certain part of the intestinal tract, it being possible to use, for example, polymeric substances and waxes as embedding materials.

The active compound or compounds may also be present in microencapsulated form, if desired with one or more of the abovementioned excipients.

Suppositories may contain the customary water-soluble or water-insoluble excipients, for example polyethylene glycols, fats, for example cocoa fat and higher esters (for example $C_{14}$ alcohol with $C_{16}$ fatty acid) or mixtures of these substances in addition to the active compound or compounds.

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound or compounds.

Powders and sprays may contain the customary excipients, for example lactose, talc, silica, hydrated alumina, calcium silicate and polyamide powder or mixtures of these substances in addition to the active compound or compounds. Sprays may additionally contain the customary propellants, for example chlorofluorohydrocarbons.

Solutions and emulsions may contain the customary excipients such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, olive oil, castor oil and sesame oil, glycerol, glycerol formal, tetrahydrofurfuryl alcohol, polyethylene glycols and fatty acid esters of sorbitan or mixtures of these substances in addition to the active compound or compounds.

For parenteral administration, the solutions and emulsions may also be present in sterile and blood-isotonic form.

Suspensions may contain the customary excipients such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound or compounds.

The formulation forms mentioned may also contain, colorants preservatives and also odor- and flavor-enhancing additives, for example peppermint oil and eucalyptus oil and sweeteners, for example saccharin.

The therapeutically active compounds should preferably be present in the abovementioned pharmaceutical preparations in a concentration from about 0.1 to 99.5, preferably from about 0.5 to 95 % by weight, of the total mixture.

The abovementioned pharmaceutical preparations may also contain further pharmaceutical active compounds in addition to the compounds according to the invention.

The abovementioned pharmaceutical preparations are prepared in a customary manner by known methods, for example by mixing the active compound or compounds with the excipient or excipients.

The present invention also includes the use of the active compounds according to the invention, and also pharmaceutical preparations which contain one or more active compounds according to the invention, in human and veterinary medicine for the prevention, amelioration and/or cure of the abovementioned diseases.

The active compounds or the pharmaceutical preparations may be administered locally, orally, parenterally, intraperitoneally and/or rectally, preferably parenterally, in particular intravenously.

In general, it has proved advantageous both in human and in veterinary medicine to administer the active compound or compounds according to the invention in total amounts from about 2.5 to about 200, preferably 5 to 150 mg/kg of body weight every 24 hours, if appropriate in the form of several individual doses, to attain the desired results.

On oral administration, the active compounds according to the invention are administered in total amounts from about 2.5 to about 200, preferably 5 to 150 mg/kg of body weight every 24 hours and on parenteral administration in total amounts of about 2.5 to about 50, preferably 1 to 25 mg/kg of body weight every 24 hours.

However, it may be necessary to deviate from the abovementioned doses, depending on the species and body weight of the subject to be treated, the nature and severity of the disease, the type of the preparation and the administration of the medicament and also the time period or interval within which the administration takes place. Thus, in some cases it may be sufficient to manage with less than the abovementioned amount of active compound, whereas in other cases the abovementioned amount of active compound must be exceeded. The optimum dosage required in each case and the type of administration of the active compounds can easily be established by any person skilled in the art on the basis of his expert knowledge.

Starting compounds and preparation examples

Example 1

1-(4-Chlorobenzoyl)-1-(3-chloro-1,2,4-triazol-1-yl)-cyclopropane

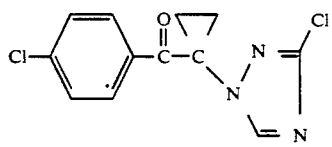

34 g (246 mmol) of potassium carbonate and 35 g (338 mmol) of 3-chloro-1,2,4-triazole are initially introduced into 130 ml of acetone under reflux and 50 g (169 mol) of 2-bromo-4-chloro-1-(4-chlorophenyl)-butan-1-one in 60 ml of acetone are added dropwise. The mixture is boiled under reflux for 8 hours, the solution is filtered off with suction from the residue and the solvent is stripped off in vacuo. The residue is taken up in ethyl acetate, washed with water and dried over sodium sulphate, and the solvent is evaporated. Chromatography on silica gel (eluent: dichloromethane) gives 42.9 g of the title compound (90% of theory) of m.p. 85° C.

Example 2

1-(3-Chloro-1,2,4-triazol-1-yl)-1-(4-fluorobenzoyl)-cyclopropane

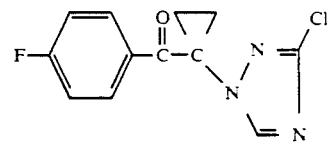

The compound from Example 2 was prepared in analogy to the procedure of Example 1.
m.p.: 84° C.

Example 3

2-(4-Chlorophenyl)-2-[1-(3-chloro-1,2,4-triazol-1-yl)-cyclopropyl]oxirane

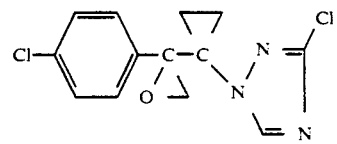

2.5 g (83 mmol) of sodium hydride (80% strength) and 17.6 g (80 mmol) of trimethylsulphoxonium iodide are initially introduced under a nitrogen atmosphere and 60 ml of absolute dimethyl sulphoxide are added dropwise at 10° C. The mixture is stirred for 1 hour at 20° C. and then 20 g (71 mmol) of 1-(4-chlorobenzoyl)-1-(3-chloro-1,2,4-triazol-1-yl)-cyclopropane dissolved in 30 ml of absolute dimethyl sulphoxide are added at 10° C. After 48 hours at 20° C., the mixture is warmed to 40° C. for 1 hour and the reaction solution is then poured into water. The mixture is extracted with ethyl acetate, the combined organic phases are washed with water and dried over sodium sulphate, and the solvent is evaporated in vacuo. 21 g of the title compound (100 % of theory) remain in the form of an oil.

$^1$H-NMR (200 MHz, CDCl$_3$): $\delta$=0.8-1.4 (m, 4H); 2.92 (d, 1H); 3.15 (d, 1H); 7.10 (d, 2H); 7.38 (d, 2H); 7.75 (s, 1H).

Example 4

1-(4-Chlorophenyl)-1-[1-(3-chloro-1,2,4-triazol-1-yl)-cyclopropyl]-2-(1,2,4-triazol-1-yl)-ethan-1-ol

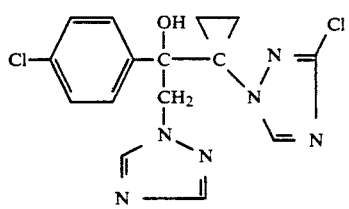

15.6 g (0.276 mol) of 1,2,4-triazole and 1.7 g (0.015 mol) of potassium tert. butoxide are initially introduced into 40 ml of abs. dimethylformamide and 21 g (0.071 mol) of 2-(4-chlorophenyl)-2-[1-(3-chloro-1,2,4-triazol-1-yl)-cyclopropyl]-oxirane in 30 ml of absolute dimethylformamide are added dropwise at 80° C. The mixture is allowed to react at 100° C. for 6 hours and the solvent is then evaporated in vacuo. The residue is taken up in ethyl acetate/toluene, the solution is washed with water and dried over sodium sulphate, and the solvent is stripped off in vacuo. Chromatography on silica gel (eluent dichloromethane/ethanol =98/2) yields 11.5 g of the title compound of m.p. 156° C.

Example 5

1-(4-Chlorophenyl)-1-[1-(3-chloro-1,2,4-triazol-1-yl)-cyclopropyl]-2-(imidazol-1-yl)-ethan-1-ol

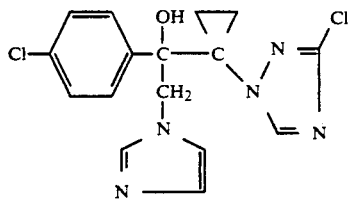

13 g (191 mmol) of imidazole and 1 g (9 mmol) of potassium tert. butoxide are initially introduced under a nitrogen atmosphere into 100 ml of acetonitrile under reflux and 18 g (61 mmol) of 2-(4-chlorophenyl)-2-[1-(3-chloro-1,2,4-triazol-1-yl)-cyclopropyl]-oxirane dissolved in 30 ml of acetonitrile are added dropwise. The mixture is allowed to react under reflux conditions for 10 hours and the solvent is then evaporated in vacuo. The residue is taken up in ethyl acetate and washed with water. The solution is dried over sodium sulphate and the solvent is removed in vacuo. Chromatographic purification on silica gel (solvent: dichloromethane/ethanol=90/10) gives 7.1 g (32% of theory) of the title compound of m.p. 231° C.

The following examples were prepared analogously to the procedure of Example 4:

Example 6

1-[1-(3-Chloro-1,2,4-triazol-1-yl)-cyclopropyl]-1-phenyl-2-(1,2,4-triazol-1-yl)-ethan-1-ol

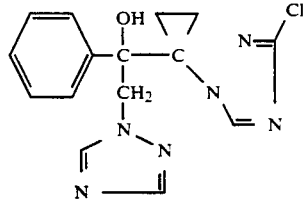

m.p.: 134° C.

Example 7

1-[1-(3-Chloro-1,2,4-triazol-1-yl)-cyclopropyl]-1-(4-fluorophenyl)-2-(1,2,4-triazol-1-yl)-ethan-1-ol

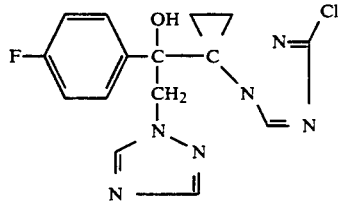

m.p.: 116° C.

Example 8

1-[1-(3-Chloro-1,2,4-triazol-1-yl)-cyclopropyl]-1-(4-methylphenyl)-2-(1,2,4-triazol-1-yl)-ethan-1-ol

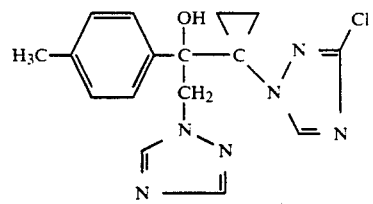

m.p.: 119° C.

Example 9

1-(4-Biphenyl)-1-[1-(3-chloro-1,2,4-triazol-1-yl)-cyclopropyl]-2-(1,2,4-triazol-1-yl)-ethan-1-ol

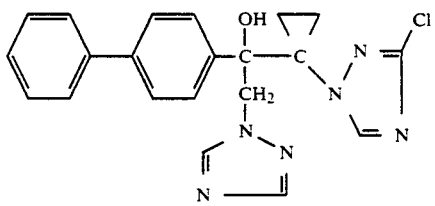

m.p.: 150° C.

Example 10

1-[1-(3-Chloro-1,2,4-triazol-1-yl)-cyclopropyl]-1-(2,4-difluorophenyl)-2-(1,2,4-triazol-1-yl)-ethan-1-ol

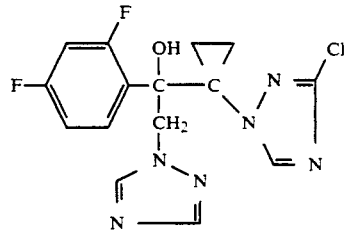

m.p.: 114° C.

Example 11

1-[1-(3-Chloro-1,2,4-triazol-1-yl)-cyclopropyl]-1-(3,4-difluorophenyl)-2-(1,2,4-triazol-1-yl)-ethan-1-ol

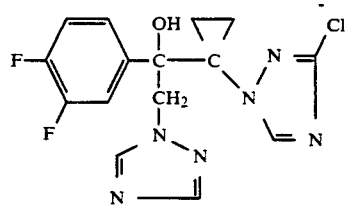

m.p.: 106° C.

Use examples

The compounds known from EP-OS 0,044,605 (A, B) and EP-OS 0,180,850 (C and D) indicated below are employed as comparison substances in the in vitro test:

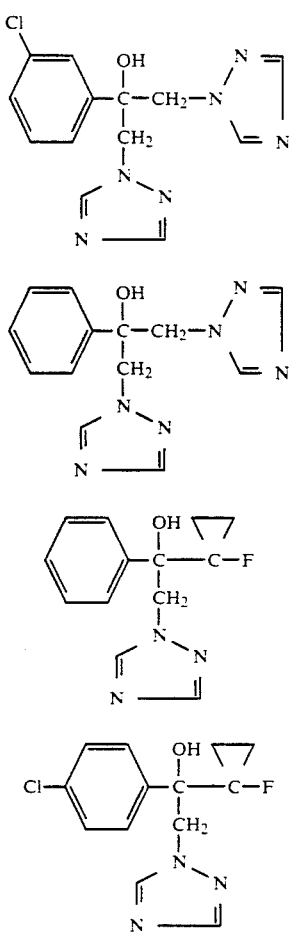

EXAMPLE A

Antimycotic in vitro activity

Experimental description

The in vitro tests were carried out in a serial dilution test using inocula of microorganisms of on average $5 \times 10^3$ to $10^4$ microorganisms/ml of substrate. The nutrient medium used was
(a) for dermatophytes and Hyphomycetes: Kimmig's test medium
(b) for yeasts:
  Meat extract-dextrose broth.

The incubation temperature was 28° to 37° C., and the incubation period was 24 to 48 hours with yeasts and 96 hours with Dermatophytes and hyphomycetes.

In this test, for example, the compounds 4, 6, 7, 8, 9, 10 and 11 according to the invention showed a better antimycotic action than the compounds (A) and (B) known from the prior art.

TABLE A

| Active Compound | Antimycotic in vitro activity | | | |
|---|---|---|---|---|
| | MIC values in μg/ml of nutrient medium | | | |
| | Tricho- phyton mentagr. | Candida albi- cans | Toru- lopsis glabrata | Asper- gillus fumigatus |
| (A) known | 32 | >64 | >64 | >64 |
| (B) known | 64 | 64 | >64 | >64 |
| Compounds according to preparation example | | | | |
| 4 | 4 | 8 | >64 | 32 |

TABLE A-continued

| Active Compound | Antimycotic in vitro activity | | | |
|---|---|---|---|---|
| | MIC values in μg/ml of nutrient medium | | | |
| | Tricho- phyton mentagr. | Candida albi- cans | Toru- lopsis glabrata | Asper- gillus fumigatus |
| 6 | 8 | 32 | >64 | 16 |
| 7 | 8 | 32 | >64 | 32 |
| 8 | 4 | 16 | >64 | 16 |
| 9 | 4 | 32 | 16 | 16 |
| 10 | 16 | 32 | >64 | 16 |
| 11 | 16 | 16 | >64 | 64 |

EXAMPLE B

Antimycotic in vivo activity (oral) in mouse condidosis

Experimental description

Mice of the SPF-CF$_1$ type were infected intravenously with $1-2 \times 10^6$ exponentially growing Candida cells which are suspended in physiological saline solution. One hour before and seven hours after infection, the animals are treated orally in each case with 10 to 100 mg/kg of body weight of the preparation.

Result

Untreated animals died on the 3rd to 6th day post-infection. The survival rate on the 6th day post-infection was about 5% in untreated control animals.

In this test, for example, the compounds, 4, 6, 7, 10 and 11 according to the invention show good to very good action, i.e. >80% surviving on the 6th day p.i.

TABLE B

| Antimycotic in vivo action (oral) in mouse candidosis | |
|---|---|
| Active compound | Action |
| (C) known | n.a. |
| (D) known | n.a. |
| Compound according to preparation examples | |
| 4 | + + + + + |
| 6 | + + + + + |
| 7 | + + + + + |
| 10 | + + + + + |
| 11 | + + + + + |

Key
+ + + + + = very good action = 90% surviving on the 6th day p.i.
+ + + + = good action = 80% surviving on the 6th day p.i.
+ + + = action = 60% surviving on the 6th day p.i.
+ + = slight action = 40% surviving on the 6th day p.i.
+ = trace action = under 40% surviving on the 6th day p.i.
n.a. = no difference to the untreated infection control.

EXAMPLE C

Antimicrobial in vivo activity (topical) in the experimental guinea-pig trichophytosis model Experimental description:

White guinea-pigs of the Pirbright white strain are infected on the shaven, non-scarified back with a micro- and macroconidia suspension of Trichophyton mentagrophytes.

The infected animals were treated topically 1 × daily with a 0.1% strength solution of the preparation according to the invention (in dimethyl sulphoxide: glycerol=1.4) beginning with the 3rd day.

Results

In untreated animals, the typical picture of a dermatophytosis with reddening, scaling and hair loss up to total integumental defect of the infection site developed within 12 days p.i.

In this test, for example, the compounds 6, 10 and 11 according to the invention show a good action.

TABLE C

Antimicrobial in vivo activity (topical) in the experimental guinea-pig trichophytosis model

| Active compound | Action |
|---|---|
| Compound according to preparation example: | |
| 6 | +++++ |
| 10 | +++++ |
| 11 | +++++ |

Explanation:

| | | |
|---|---|---|
| +++++ = | very good action = | no sign of infection on the 12th to 15th day p.i. |
| ++++ = | good action = | slight reddening, isolated scaling |
| +++ = | action = | reddening, scaling without hair loss |
| ++ = | slight action = | reddening, scaling, hair loss |
| + = | trace action = | relatively extensive hair loss, inflammatory skin reaction. |

Example D/formulations
1) Solution:

| | |
|---|---|
| active compound according to formula (I): | 10 g |
| alcohol, pure (96% strength): | 300 g |
| isopropyl myristate: | 526 g |
| | 836 g |

2) Cream:

| | |
|---|---|
| active compound according to formula (I): | 10 g |
| Arlacel 60: (sorbitan monostearate) | 20 g |
| Tween 60: (polyoxyethylene(2)sorbitan monostearate) | 15 g |
| spermaceti, synthetic: (mixture of esters of saturated C14-C18 fatty acids and C14-C18 fatty alcohols) | 30 g |
| Lanette O: | 100 g |
| Eutanol G: (2-octyl-dodecanol) | 135 g |
| benzyl alcohol: | 10 g |
| water, demineralized: | 680 g |
| | 1000 g |

What is claimed is:

1. An azolyl-cyclopropyl-azolylmethylcarbinol compound of the formula

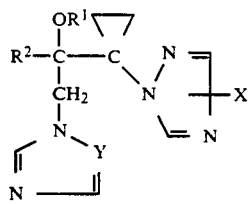

wherein
R¹ is hydrogen,
R² is phenyl which is substituted by one or two substituents selected from the group consisting of fluorine, chlorine, and methyl,
X is chlorine and
Y is a nitrogen atom.

2. The azolyl-cyclopropyl-azolylmethyl-carbinol compound according to claim 1, which is 1-(4-chlorophenyl)-1-[1-(3-chloro-1,2,4-triazol-1-yl)-cyclopropyl]-2-(1,2,4-triazol-1-yl)-ethan-1-ol having the formula

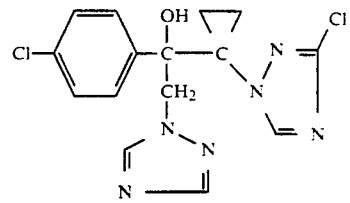

3. The azolyl-cyclopropyl-azolylmethyl-carbinol compound according to claim 1, which is 1-[1-(3-chloro-1,2,4-triazol-1-yl)-cyclopropyl]-1-(4-fluorophenyl)-2-(1,2,4-triazol-1-yl)ethan-1-ol having the formula

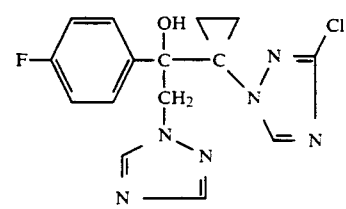

4. The azolyl-cyclopropyl-azolylmethyl-carbinol compound according to claim 1, which is 1-[1-(3-chloro-1,2,4-triazol-1-yl)-cyclopropyl]-1-(4-methylphenyl)-2-(1,2,4-triazol-1-yl)-ethan-1-ol having the formula

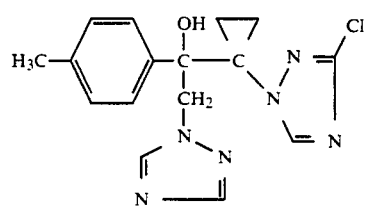

5. The azolyl-cyclopropyl-azolylmethyl-carbinol compound according to claim 1, which is 1-[1-(3-chloro-1,2,4-triazol-1-yl)-cyclopropyl]-1-(2,4-difluorophenyl)-2-(1,2,4-triazol-1-yl)-ethan-1-ol having the formula

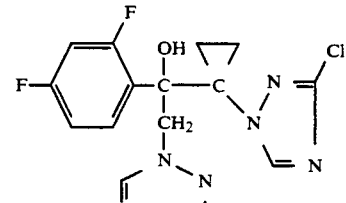

6. The azolyl-cyclopropyl-azolylmethyl-carbinol compound according to claim 1, which is 1-[1-(3-chloro-1,2,4-triazol-1-yl)-cyclopropyl]-1-(3,4-difluorophenyl)-2-(1,2,4-triazol-1-yl)-ethan-1-ol having the formula

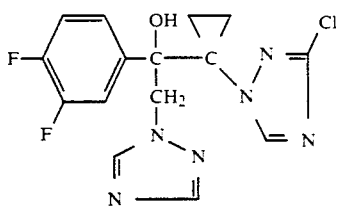

7. A pharmaceutical composition comprising an effective amount therefor of an azolylcyclopropyl-azolylmethyl carbinol compound according to claim 1 together with an inert pharmaceutical excipient.

8. A medicament in dosage unit form comprising an antimycotically effective amount of an azolyl-cyclopropylazolylmethyl carbinol compound according to claim 1 either with alone or in admixture with an inert pharmaceutical excipient.

9. A medicament according to claim 8 in the form of tablets, coated tablets, capsules, pills, granules. suppositories, solutions, suspension, emulsions. pastes. ointments, gels, creams, lotions, powders or sprays.

10. A method of combating mycoses in warm blooded animals which comprises administering to said animal antimycotically effective amount of a compound according to claim 1 either alone or in admixture with an inert excipient or in the form of a medicament.

* * * * *